(12) United States Patent
McLeod

(10) Patent No.: US 10,937,155 B2
(45) Date of Patent: Mar. 2, 2021

(54) IMAGING SYSTEM AND METHOD FOR GENERATING A MEDICAL IMAGE

(71) Applicant: General Electric Company, Schenectady, NY (US)

(72) Inventor: Kristin McLeod, Horten (NO)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 33 days.

(21) Appl. No.: 16/215,067

(22) Filed: Dec. 10, 2018

(65) Prior Publication Data

US 2020/0184634 A1    Jun. 11, 2020

(51) Int. Cl.
| | |
|---|---|
| *G06T 7/00* | (2017.01) |
| *G06T 11/00* | (2006.01) |
| *G01R 33/48* | (2006.01) |
| *G01R 33/46* | (2006.01) |
| *G06T 11/60* | (2006.01) |
| *G16H 30/20* | (2018.01) |

(52) U.S. Cl.
CPC .......... *G06T 7/0012* (2013.01); *G06T 11/001* (2013.01); *G06T 11/60* (2013.01); *G16H 30/20* (2018.01); *G06T 2207/10081* (2013.01); *G06T 2207/10088* (2013.01); *G06T 2207/10116* (2013.01); *G06T 2207/10132* (2013.01); *G06T 2207/30168* (2013.01)

(58) Field of Classification Search
CPC combination set(s) only.
See application file for complete search history.

(56) References Cited

U.S. PATENT DOCUMENTS

| | | | |
|---|---|---|---|
| 6,725,074 B1* | 4/2004 | Kastle | A61B 5/14551 600/323 |
| 2007/0100126 A1* | 5/2007 | Chen | B01J 8/388 528/308 |
| 2008/0130970 A1* | 6/2008 | Niemeyer | G06T 7/0012 382/128 |
| 2016/0038122 A1* | 2/2016 | Lee | A61B 8/523 600/408 |
| 2018/0101644 A1* | 4/2018 | Hammes | G06K 9/6201 |
| 2018/0198702 A1* | 7/2018 | Li | H04L 49/252 |
| 2018/0271614 A1* | 9/2018 | Kunio | A61B 90/37 |
| 2018/0310920 A1 | 11/2018 | Specht et al. | |
| 2019/0122073 A1* | 4/2019 | Ozdemir | A61B 6/5217 |
| 2019/0192229 A1* | 6/2019 | Berlin | A61B 8/488 |
| 2019/0266716 A1* | 8/2019 | Rothberg | G06T 7/0002 |
| 2019/0287241 A1* | 9/2019 | Hill | G06T 7/0012 |
| 2019/0307393 A1* | 10/2019 | Lotz | A61B 5/4566 |

* cited by examiner

*Primary Examiner* — Wesner Sajous
(74) *Attorney, Agent, or Firm* — The Small Patent Law Group LLC; Dean D. Small

(57) ABSTRACT

A method that includes acquiring image data, and determining a quality level for a measurement presented in a medical image. The quality level is based on the acquired image data. The method also includes generating the medical image including a measurement indicator based on the quality level, and displaying the medical image on a display device.

19 Claims, 6 Drawing Sheets

IMAGING SYSTEM AND METHOD FOR GENERATING A MEDICAL IMAGE

BACKGROUND OF THE INVENTION

This disclosure relates generally to automated imaging systems and methods for color-coding and labeling images of an automated imaging system to indicate the quality/confidence level of a component in the imaging results.

Clinical imaging procedures are oftentimes used to acquire quantitative or qualitative information from a scanned area. Computer tomography scans (CT scans), magnetic resonance imaging scans (MRI scans), ultrasound scans, X-Ray scans, or the like present visual representations to a user of the human anatomy. Improvements in these systems, including through artificial intelligence and reinforcement learning techniques have led to the formation of algorithms to analyze imaging data and provide autonomous measurements and diagnosis for these systems. As an example, automated ultrasound systems may utilize different images of a region of interest (ROI) to form a combined image that identifies the human anatomy being scanned and imaged. In making the identification, the automated ultrasound system can take measurements, trace image objects, provide labels related to image objects, or the like and then display a visual component to a clinician related to the identification. As examples, measurement numbers may be displayed, borders may be traced around identified objects in the scan, labels may be associated with the identified objects, or the like to provide a visual representation to the clinician of the scanned anatomy.

Reliability and reproducibility of measurements, tracing, labels, objects, or the like, are of great importance and thus automatic methods offer the possibility to perform tasks without objectivity. However, such methods typically give the user the outcome and no additional information.

In particular, trusting fully automatic systems can be a challenge for clinicians when they have no way to understand why the medical device gives an output that they do not agree with. Specifically, in an automated medical device application, either measurements, tracing, labels, or the like are shown on an image without computation of the certainty or quality of the measurements, tracing, labels, or the like. Alternatively, often an automated image will not provide measurements, tracing, objects, labels, or the like when a threshold of certainty is not provided. Without understanding the certainty or quality of the measurements, tracing, labeling, or the like, a clinician must make assumptions about the quality of each, and either take a tedious and time consuming review of the measurements, tracing, labeling, or the like that is unneeded because the measurements, tracing, labeling, or the like have a great level of certainty or quality. Alternatively, a clinician assumes that the measurements, tracing, labeling, or the like are of high quality or certainty and does not spend an adequate amount of time reviewing the automated image and information, leading to incorrect readings and outcomes based on an image with substandard quality.

BRIEF DESCRIPTION OF THE INVENTION

The above-mentioned shortcomings, disadvantages and problems are addressed herein which will be understood by reading and understanding the following specification.

In one or more embodiments, a method that includes acquiring image data, and determining a quality level for a measurement presented in a medical image, the quality level based on the acquired image data. The method includes generating the medical image including a measurement indicator based on the quality level, and displaying the medical image on a display device.

In one or more embodiments, a method that includes acquiring image data, and determining image parameters from the acquired image data. The method also includes determining a first quality level for a first measurement presented in a medical image, the first quality level based on the determined image parameters, and determining a second quality level for a second measurement presented in the medical image, the second quality level based on the determined image parameters. The method also includes generating a first measurement indicator based on the first quality level, and generating a second measurement indicator based on the second quality level. The method also includes generating the medical image including the first measurement indicator and the second measurement indicator, and displaying the medical image on a display device.

In one or more embodiments, a non-transitory computer readable medium is provided. The non-transitory computer has stored thereon, a computer program having at least one code section, said at least one code section being executable by a machine for causing said machine to perform one or more steps. The steps include acquiring image data, and determining a quality level for a measurement presented in a medical image, the quality level based on the acquired image data. The steps also include generating the medical image including a measurement indicator based on the quality level, and displaying the medical image on a display device.

DETAILED DESCRIPTION OF THE INVENTION

Figure 1:
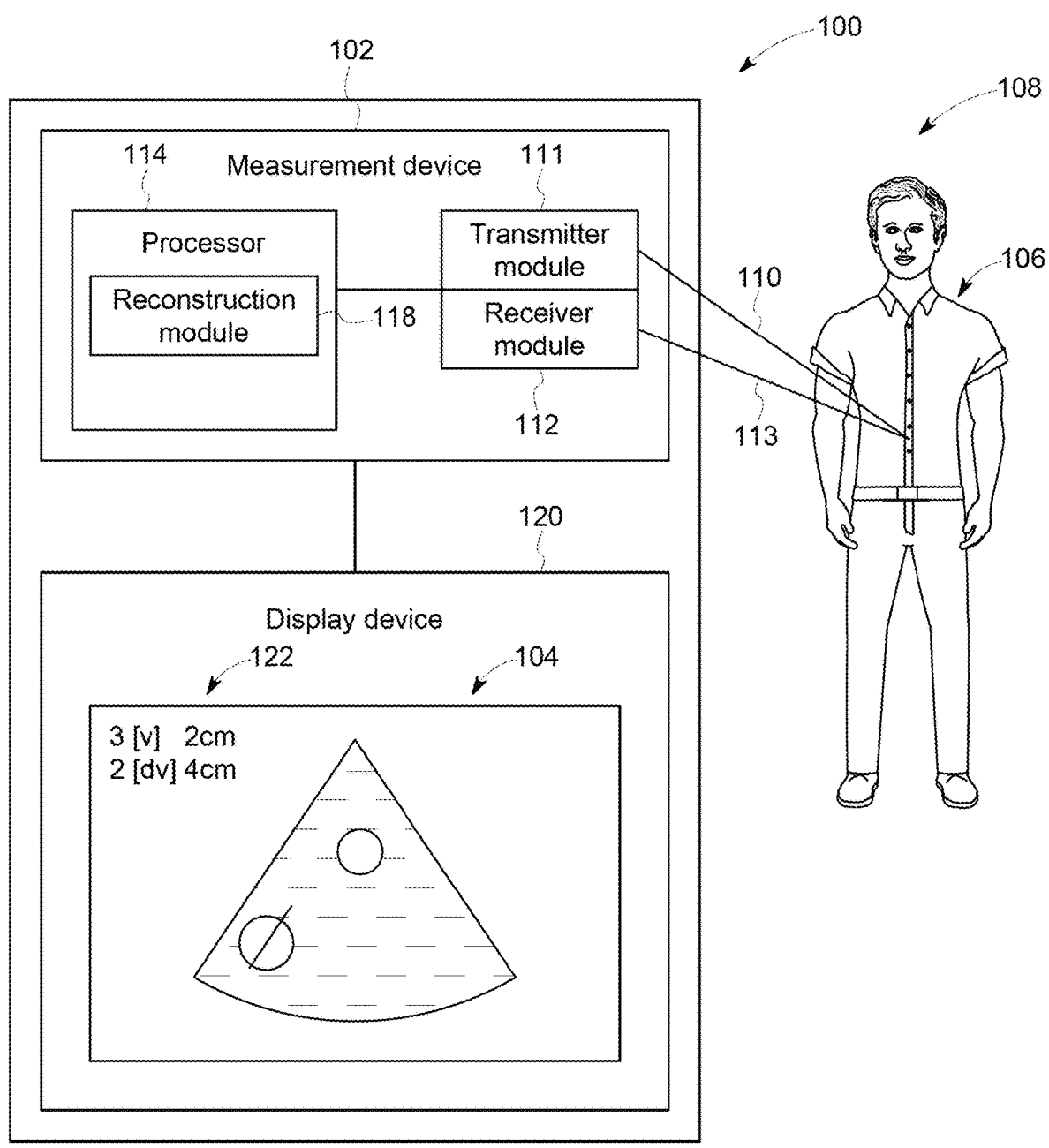
FIG. 1 illustrates a schematic diagram of an imaging system in accordance with an embodiment.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

FIG. 1 is a schematic diagram of an imaging system 100 in accordance with an embodiment that receives image data related to the anatomy of a patient, and from the image data displays a visual representation related to the anatomy being examined. Representative imaging systems include CT systems, MRI systems, ultrasound systems, X-Ray systems, or the like. The imaging system 100 may be a console based system, a laptop, a handheld or hand-carried system, or any other configuration.

For each imaging system 100, a measurement device 102 obtains image data in order to create an image 104 of the anatomy 106 of a patient 108. In exemplary embodiments the measurement device 102 includes CT scanners that emit X-rays, MRI scanners that create a magnetic field and emit radio frequency pulses, probe devices that emit pulsed ultrasonic signals, electronic devices that utilize electronic signals, or the like.

For each modality, the measurement device 102 bombards a region of the anatomy 106 of the patient 108 with a signal 110 from a transmitter module 111, including x-rays, other electromagnet waves, sound waves, or the like. The measurement device 102 includes a receiver module 112 that receives a feedback signal 113 from the signals 110 to form the image data. The terms "scan" or "scanning" may also be used in this disclosure to refer to acquiring data through the process of transmitting and receiving signals. The terms "data" and "image data" and "imaging data" may be used in this disclosure to refer to either one or more datasets acquired with a measurement device 102 of an imaging system 100.

In example embodiments, the image data includes segmented images of a region of interest where each segmented image is taken from a different position, or view of the anatomy 106 being examined. The receiver module 112 then transmits the image data to a processor 114 for reconstruction of an image 104 from the image data by a reconstruction module 118 of the processor 114. The reconstructed image 104 in example embodiments can be one-dimensional (1D), two-dimensional (2D), three-dimensional (3D), or four-dimensional (4D). The processor 114 displays the image 104 on a display device 120 of the measurement device 102 for use by a clinician.

The processor 114 may be one or more processors and may be within the measurement device 102 or coupled remotely to the measurement device 102 to be in electronic communication with the measurement device 102. For purposes of this disclosure, the term "electronic communication" may be defined to include both wired and wireless connections. The processor 114 thus includes a computer readable medium having stored thereon, a computer program having at least one code section, said at least one code section being executable by a machine for causing said machine to perform steps described herein. This includes at least the methodology as described in relation to FIG. 2.

Specifically, the processor 114 controls the transmission of the signal 110 and receives the feedback signal 113 from the scanned anatomy 106 via the receiver module 112. The processor 114 can include a beamformer in example embodiments including software components, including a graphics processing unit (GPU), a microprocessor, a central processing unit (CPU), a digital signal processor (DSP), or any other type of processor capable of performing logical operations.

The processor 114 in an example may control hardware to acquire ultrasound data. In one example the processor 114 is in electronic communication with the display device 120, and the processor 114 processes the imaging data into one or more images 104 for display on the display device 120.

The processor 114 may also include a central processing unit (CPU) according to an embodiment. According to other embodiments, the processor 114 may include other electronic components capable of carrying out processing functions, such as a digital signal processor, a field programmable gate array (FPGA), a graphics processing unit (GPU) or any other type of processor. According to other embodiments, the processor 114 may include multiple electronic components capable of carrying out processing functions. For example, the processor 114 may include two or more electronic components selected from a list of electronic components including: a CPU, a digital signal processor (DSP), a FPGA, and a GPU.

According to another embodiment, the processor 114 may also include a complex demodulator (not shown) that demodulates radio frequency (RF) data and generates raw data. In another embodiment the demodulation can be carried out earlier in the processing chain. The processor 114 may be adapted to perform one or more processing operations according to a plurality of selectable modalities on the imaging data. The imaging data may be processed in real-time during a scanning session as the echo signals are received. For the purposes of this disclosure, the term "real-time" is defined to include a procedure that is performed without any intentional delay. Real-time frame or volume rates may vary based on the size of the region or volume from which data is acquired and the specific parameters used during the acquisition. The imaging data may be stored temporarily in a buffer (not shown) during a scanning session and processed in less than real-time in a live or off-line operation.

Some embodiments of the invention may include multiple processors (not shown) to handle the processing tasks. For example, a first processor may be utilized to demodulate and decimate a RF signal while a second processor may be used to further process the imaging data prior to display as an image. It should be appreciated that other embodiments may use a different arrangement of processors. Or, the processing functions attributed to the processor 114 may be allocated in a different manner between any number of separate processing components.

The reconstruction module 118, in example embodiments includes algorithms, including reinforcement learning algorithms, artificial intelligence algorithms, or the like to analyze the image data to display measurement parameters 122 in the reconstructed image 104. Measurement parameters 122 include numerical measurement information such as diameter, area, volume, flow rate, temperature, or the like; tracing information including the outlining of borders of an identified object of the anatomy 106 of the patient 108; labels including text boxes that identify information including what objects in an image represent, or providing measurement data and information about an object or mass in an image; or the like.

In various embodiments of the present invention, the reconstruction module may process the imaging data by other or different mode-related modules by the processor 114 (e.g., B-mode, Color Doppler, M-mode, Color M-mode, spectral Doppler, Elastography, TVI, strain, strain rate, and the like) to form varying images or data. For example, one or more modules may generate B-mode, color Doppler, M-mode, color M-mode, spectral Doppler, Elastography, TVI, strain, strain rate and combinations thereof, and the like. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in an image memory, from which the images are read and displayed.

The display 120 may be used to control the input of patient data, or to select various modes, operations, and parameters, and the like. The display 120 may include a one or more user input devices such as a keyboard, hard keys, a touch pad, a touch screen, a track ball, rotary controls, sliders, soft keys, or any other user input devices.

Figure 2:
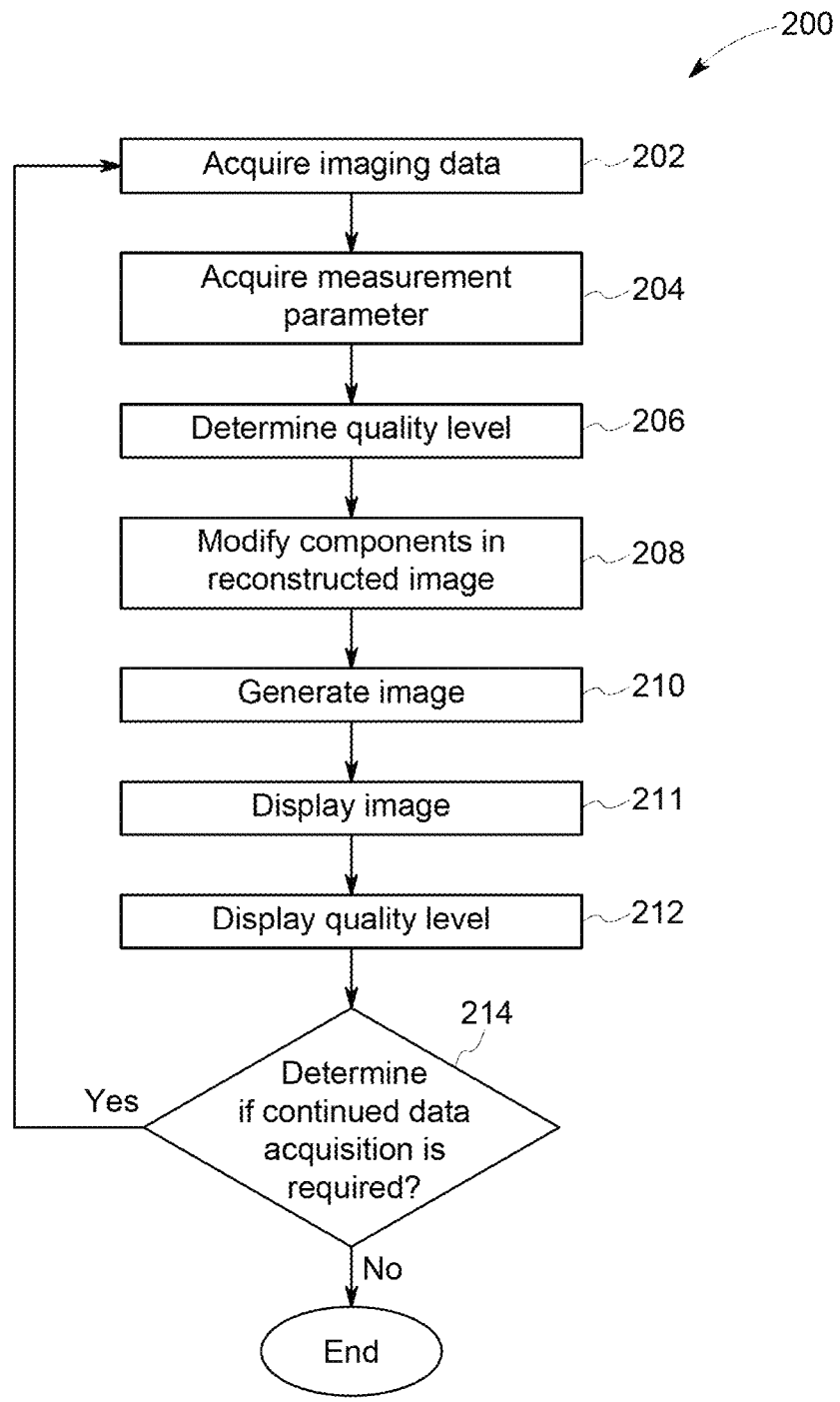
FIG. 2 is a flow chart in accordance with an embodiment.

FIG. 2 is a flow chart of a method 200 in accordance with an exemplary embodiment. The individual blocks of the flow chart represent steps that may be performed in accordance with the method 200. Additional embodiments may perform the steps shown in a different sequence and/or additional embodiments may include additional steps not shown in FIG. 2. The technical effect of the method 200 is the display of an image generated from imaging data that include measurements, tracing, labels, or the like and an associated indicator at least one of the measurements, tracing, labels, or the like. The associated indicator can include color-coding, numerals, letters, or the like to represent the quality, fidelity, or associated confidence level of the measurements, tracing, labels, or the like.

FIG. 2 will be described in accordance with an exemplary embodiment where the method 200 is performed by the imaging system 100 shown in FIG. 1. At 202, the processor 114 transmits a signal 110 to acquire imaging data from a region of interest of an anatomy 106 of a patient 108. The imaging data may include one-dimensional (1D) data, two-dimensional (2D) data, three-dimensional (3D) data, four-dimensional (4D) data or segmented image data. The imaging data may be acquired and displayed in real-time as part of a "live" imaging procedure. Or, according to other embodiments, the imaging data may be acquired during a first discrete period of time, processed, and then displayed after processing.

At step 204, the processor 114 acquires measurement parameters during the process of acquiring the imaging data. Each measurement parameter may be any parameter that is correlated with the quality, or confidence of the acquisition and component within the image including image parameters. Components of the image include numerical characteristics such as volume, diameter, and the like, bordering of objects, labeling of objects, or the like. Acquiring the measurement parameter may include calculating the measurement parameter from the imaging data according to some embodiments, while in other embodiments, acquiring the measurement parameter may include acquiring a measurement parameter based on imaging data that is not from the image data. For example, the measurement parameter may be acquired with a sensor. The measurement parameter may, for instance, include a noise level of the acquisition, an amount of probe motion, a frame-consistency-over-time metric, a signal intensity, a correctness-of-view metric, a correctness of a flow spectral waveform, or any other parameter associated with measurement quality. In general, a lower noise level is correlated with higher measurement quality, a lower amount of probe motion is correlated with higher measurement quality, and a higher frame-consistency-over-time is correlated with higher measurement quality. The correctness-of-view metric may be calculated by comparing acquired image frames with a standard view using image correlation techniques. Some embodiments may employ deep learning and/or neural networks to determine how closely an acquired image frame matches a standard view.

At step 206, the processor 114 determines the image quality level of all of the components of the image based on the measurement parameter acquired at step 204. According to some embodiments, the processor 114 may determine the image quality level based on two (2) or more different measurement parameters. Or, according to other embodiments, the processor 114 may determine the quality level based on only a single measurement parameter. In example embodiments, the determination is made utilizing algorithms, including reinforcement learning algorithms, artificial intelligence algorithms, and the like. Specifically, in examples, only measurement parameters are utilized in making the determination, without use of historical data, with rewards provided for correct diagnosis and greater weights provided to variables resulting in accurate measurements. As an example, when noise level and signal intensity are the measurement parameters utilized, if the noise level associated with a measurement indicates a poor quality level, but the signal intensity associated with a measurement indicates a high quality level, a medium quality level is provided. If during this iteration, a clinician deems the measurement to be accurate, during a next iteration more weight is provided to the signal intensity than the noise level in determining the quality level such that a noise level providing a medium quality level and a signal intensity providing a high quality level results in a high quality level for the measurement.

Next, at step 208, the processor 114 modifies each component in the reconstructed image to illustrate quality level of each component of the image. In one example embodiment, each component is color-coded with each different color or shading indicating a different level of quality. Specifically, the processor 114 may select from at least a first color and a second color, where the second color is different than the first color. According to an embodiment, the first color may represent a first quality level and the second color may represent a second quality level. According to an embodiment, the first color may represent a first range of quality levels and that second color may represent a second range of quality levels, where the second range does not overlap with the first range. The first color may be, for example, green, and the first ranges of quality levels may represent quality levels that are considered acceptable. The second color may be, for example, red, and the second range of quality levels may represent quality levels that are unacceptable.

According to other embodiments, the processor 114 may select from more than two colors representing more than two discrete ranges of quality levels. For example, a first color, such as green, may represent a first quality level; a second color, such as yellow, may represent a second quality level; and a third color, such as red, may represent a third quality level. Or, the first color may represent a first range of quality levels, the second color may represent a second range of quality levels, and the third color may represent a third range of quality levels. The first range of quality levels, the second range of quality levels, and the third range of quality levels may each be discrete, non-overlapping ranges according to an embodiment. According to other embodiments, more than three different colors may be used to represent various quality levels or various ranges of quality levels.

According to an embodiment using three colors, green may be the first color and it may be used to represent a quality level that is high, red may be the second color and it may be used to represent a quality level that is low, and yellow may be the third color and it may be used to represent a quality level that is medium (i.e., in between the high quality level and the low quality level). The quality levels (i.e., high, medium and low, according to an embodiment) may be preset on the processor 114 at the factory or they may be user definable. The user may, for instance, assign a range of measurement parameter values to each quality level. Likewise, the user may assign various quality levels to quality values or the user may define a range of quality levels associated with each color.

In an alternative embodiment, the quality level of a component is expressed on a numeric scale, such as, for example 1-10. Thus, numbers 1-3 can represent a low quality level that a clinician recognizes as a poor quality level and will ensure to take a closer, or more detailed look at the component during review. Similarly, numbers 8-10 can represent a high quality level. Thus, when a clinician observes a component with an 8-10 quality level, the clinician can more quickly and efficiently scan through the component with confidence the image measure, trace, label, diagnosis, or the like generated by the automated measuring device 102 has a high probability of being accurate.

Next, at step 210, the processor 114 generates an image based on the imaging data. The image may be a 1D image, a 2D image, a 3D image or a 4D image. The image may be generated from any mode of imaging data. For example, the image may be a B-mode image, a Color Doppler image, a M-mode image, a Color M-mode image, a spectral Doppler image, an Elastography image, a TVI image, or any other type of image generated from imaging data. The imaging data may be acquired, and the image may be displayed in real-time as part of a "live" imaging procedure. According to embodiments, the image may be a still frame generated from the imaging data. According to other embodiments, the processor 114 may generate images from two or more different imaging modes at step 210 based on the imaging data. In an IVC mode, the processor 114 may generate both a B-mode image and an M-mode image based on the ultrasound data. At step 211, the processor 114 displays the image on the display device 120.

At step 212, the processor 114 displays a quality level associated with each component in the image 104. As described above, the quality level may be a color-coded scheme with each color, or shade of color representing a different level of quality. Alternatively, numbers, letters, or the like may be used to communicate to a clinician the quality of the target object in the image for the purposes of review of the image and diagnosis by the clinician. Examples of types of information that may be displayed will be described hereinafter with respect to FIGS. 3-6.

At step 214, the processor 114 determines if it is desired to continue acquiring imaging data. If it is desired to continue acquiring imaging data, the method 200 may repeat steps 202, 204, 206, 208, 210, 211, and 212. According to an embodiment where the image 104 is a live image, the steps 202, 204, 206, 208, 210, 211, 212, and 214 may be iterated many times during the acquisition and display of the live image. The steps 204, 206, 208, 210, 211, 212, and 214 may, for instance, all be performed multiple times during the process of acquiring the imaging data at step 202.

Figure 3:
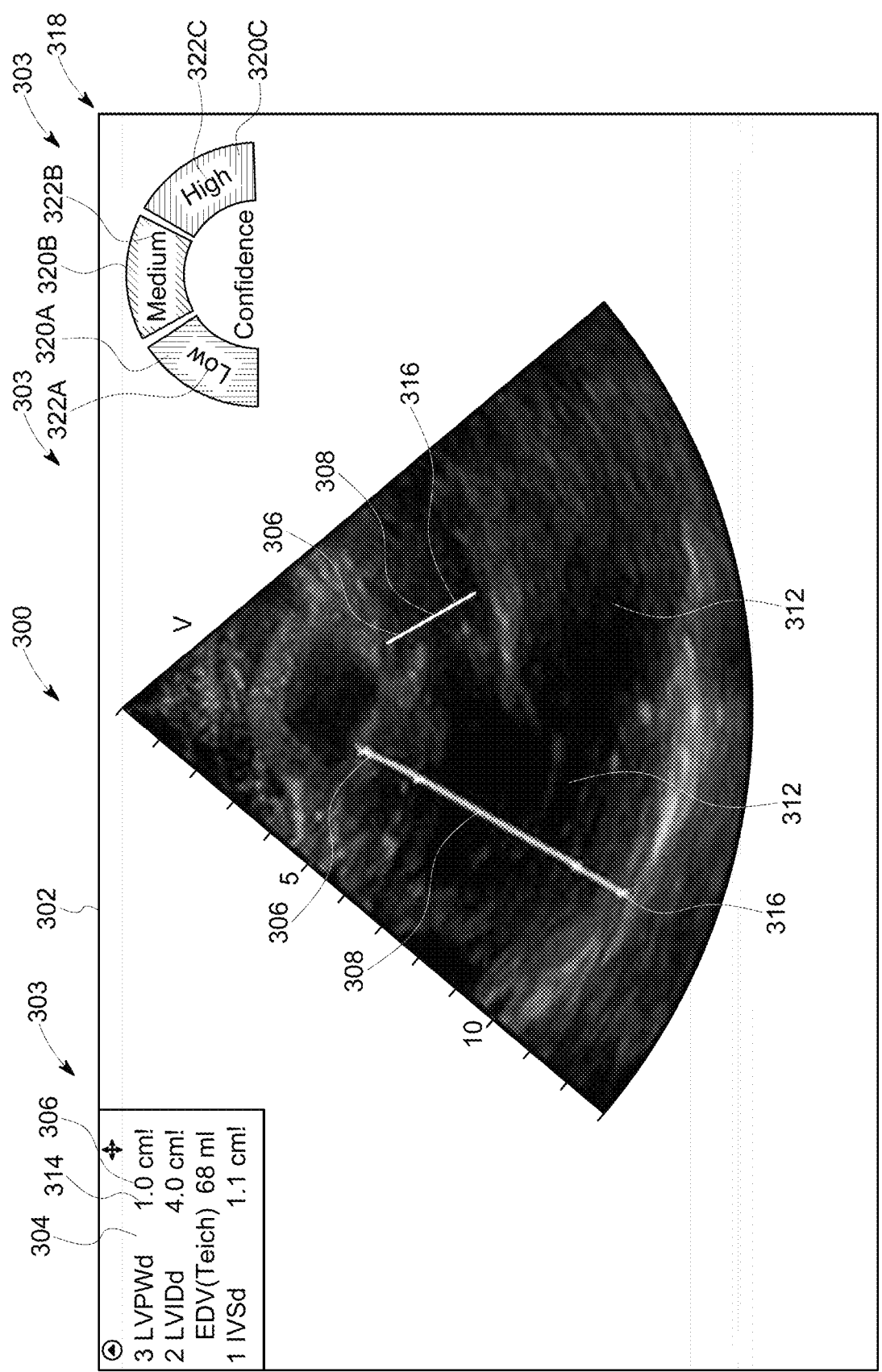
FIG. 3 is a schematic representation of an image in accordance with an embodiment.

FIG. 3 illustrates a schematic representation of a medical image 300 of a patient's anatomy in accordance with an example embodiment. The medical image may be generated by an ultrasound device, CT device, X-ray device, MRI device, or the like. The image 300 in one example is displayed on a display 302, that in one embodiment is display 120 of the imaging system 100 of FIG. 1. The image 300 includes components 303 including a text box 304, measurements 306 and measurement indicators 308.

In one embodiment, the border of the text box 304 is not on the display 302. In other embodiments, only the measurements 306, and measurement indicators 308 are displayed on the display 302 and they are not within a text box 304.

Measurements 306 include numerical values associated with a patient such as fluid levels, fluid concentrations, volume measurements, beats per minute, and the like. These include numerical values that vary or fluctuate over time, or are static. Additionally, measurements 306 also include object identification such as the shape and/or size of an object 312 identified within the medical image 300.

In the exemplary embodiment of FIG. 3, the measurement indicators 308 include measurement indicia 314 and identification lines 316. Alternatively, icons, borders, shapes, or the like could be utilized to represent the different measurements 306. In one example the object border is a line that encloses an object in an image to provide a perimeter around an object. The object 312 in different embodiments include organs, fetuses, bones, tissue, and the like. The object border includes object borders that are identified by a clinician and manually illustrated on an image with an illustration device, and an object border generated by the imaging system and formed by the one or more processors on the image. In the case when a manual object border is provided, the clinician may input through an input device or interface the certainty of the object border based on the experience of clinician. In such cases an additional indicator, such as a dashed line, striped color pattern, and the like, may be utilized to indicate the object border has been manually placed. Alternatively, when the imaging system provides the object border, the imaging system may utilize segmented images to arrive at the object border as described herein.

The measurement indicator 308 may also include measurement indicia 314. Measurement indicia 314 includes any text values associated with a measurement that appear on an image. In one example, the measurement indicia 314 include numerical values associated with a patient such as fluid levels, fluid concentrations, volume measurements, beats per minute, and the like. These include numerical values that vary or fluctuate over time, or are static. Specifically, the measurement indicia 314 provide a numerical value that is displayed on the image associated with a measurement made by the imaging system. This numerical value can be received from a sensor, calculated utilizing an algorithm, and the like.

The measurement indicators 308 may also include identification lines 316. In particular, the identification lines 316 span objects 312 that in this exemplary embodiment are represented by dark spots on the image 300. The objects 312 in different embodiments include organs, fetuses, bones, tissue, and the like.

In one example, when the medical image 300 is being reconstructed in a manner as described in relation to FIG. 2, image parameters associated with each measurement are utilized to generate each measurement indicator 308. Image parameters are measurement parameters that can include information related to signal strength, interference measurements, signal direction, or the like. While the examples provided herein discuss a first measurement and second measurement, or first quality level and second quality level, or first measurement indicator and second measurement indicator, these are examples and additional measurements, measurement indicators, quality levels, and the like are also contemplated.

In one example embodiment, a standard deviation of the image parameters is calculated and compared to one or more threshold standard deviations to determine the quality level. Thus, if the standard deviation of the image parameters exceeds a first threshold value, a first quality level is presented and a measurement indicator 308 is generated that indicates to a clinician or user the first quality level. In one example a first color, such as red, is utilized to represent the first quality level of the measurement 306 in the medical image 300. Then, in an embodiment when the first measurement indicator is an identification line 316, the identification line 316 appears in red on the screen.

In the example, if the standard deviation is below the first threshold value, but above a second threshold value, a second quality level is presented, and first measurement indicator 308 is generated to represent the second quality level. In one example embodiment a second color, such as yellow, is utilized to represent the second quality level in the medical image 300. Then, in an embodiment when the first measurement indicator 308 is an identification line 316, the identification line 316 appears in yellow on the screen. Similarly, if the standard deviation is below the first threshold value, and second threshold value, a third quality level is presented, and the first measurement indicator 308 is generated to represent the third quality level. In one example embodiment a third color, such as green, is utilized to represent the third quality level in the medical image 300. Then, in an embodiment when the first measurement indicator is an identification line 316, the identification line 316 appears green. Therefore, the different quality levels each represent a range of quality level that can be identified by a clinician or user when utilizing the medical image 300. Thus, if a clinician understands the quality level corresponding to each color, or measurement indictor, the clinician is able to treat the corresponding measurements 306 accordingly.

In another example embodiment, in a similar manner, the image parameters are compared to historical image parameters to determine the quality level based on differences between the historical image parameters and determined image parameters. In yet another example, the quality level is based on the amount of image data acquired. Thus, in an instance where the automated measurement device has indicated on the image 300 a measurement 306 is provided, but the measurement indictor 308 is a predetermined color corresponding to a poor quality, such as red, a clinician knows the quality, certainty, or fidelity of that determination is reduced. A closer exam may be undertaken resulting in the clinician determining the measurement device is incorrect, preventing an incorrect evaluation. Similarly, frustrations of a clinician can be reduced as the clinician upon seeing an incorrect evaluation can realize the reading or image itself had a poor quality level and that in other instances when the machine imaging has a better quality level, the measurement device is accurate and an effective tool to be used.

In another example embodiment, the quality level is based on measurement parameters or image parameters as determined by algorithms, including reinforcement learning algorithms, artificial intelligence algorithms, and the like. Specifically, in examples, only measurement parameters are utilized in making the determination, without use of historical data, with rewards provided for correct diagnosis and greater weights provided to variables resulting in accurate measurements. As an example, when noise level and signal intensity are the measurement parameters utilized, if the noise level associated with a measurement indicates a poor quality level, but the signal intensity associated with a measurement indicates a high quality level, a medium quality level is provided. If during this iteration, a clinician deems the measurement to be accurate, during a next iteration more weight is provided to the signal intensity than the noise level in determining the quality level such that a noise level providing a medium quality level and a signal intensity providing a high quality level results in a high quality level for the measurement.

In another example embodiment, a quality factor indicator 318 is also displayed in the image 300 on the display 302. While illustrated as located in the top right corner of the image, the quality factor indicator 318 can be positioned in other locations on the image 300. The quality factor indicator 318 includes arcuate sections 320A-C. While illustrated as arcuate sections 320A-C, other shapes, or items, such as numbers, letters, or the like, may similarly be utilized.

In one exemplary embodiment, each arcuate section 320A-C is provided with a different color and a text indicator 322A-C that conveys to a user the quality level that color represents in the image 300. In an example, the color red has a text indicator 322A of "low", indicating that red presented on the image 300 to identify an image component measurement, trace border, object, or the like has a low quality level, or is poor, and thus a clinician should spend additional time reviewing the measurement, or object 312 to ensure accuracy of the measurement device determination. Specifically, low and/or poor quality levels as described herein are above or below a predetermined first threshold level based on the quality level determined from the measurement parameters.

Similarly, the second text indicator 322B can be "medium" and the color of the second arcuate section 320B can be yellow, while the third text indicator 322C is "high" while the color of the third arcuate section 320C is green. Specifically, medium and/or average quality levels as described herein are above the predetermined first threshold level, but below a predetermined second threshold level, or vice versa, based on the quality level determined from the measurement parameters. High and above average quality levels as described herein are above or below the predetermined second threshold level based on the quality level determined from the measurement parameters.

Therefore, each color is associated with a different quality level, allowing a clinician to immediately understand the potential accuracy of measurements. Thus, in an example where a first identification line 316 is a first color, and the second identification line 316 is a second color, the clinician need only review the quality factor indicator 318 and match the color of an arcuate section 320A-C and matching text indicator 322A-C on the corresponding arcuate section 320A-C to make the determination regarding the meaning of the color of each identification line 316.

Figure 4:
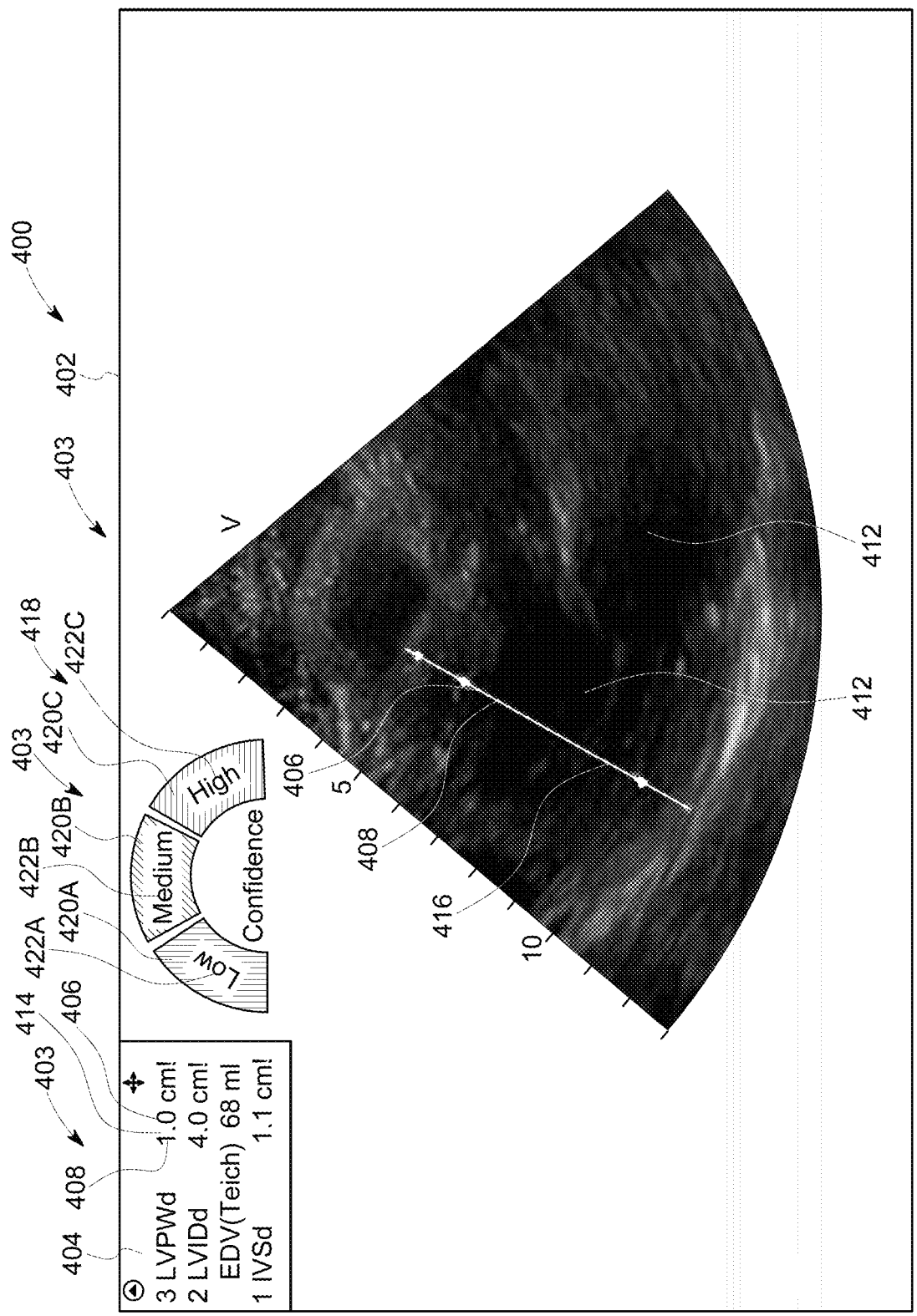
FIG. 4 is a schematic representation of an image in accordance with an embodiment.

FIG. 4 illustrates a schematic representation of a medical image 400 of the patient's anatomy in accordance with an example embodiment. The medical image may be generated by an ultrasound device, CT device, X-ray device, MRI device, or the like. The image 400 in one example is displayed on a display 402, that in one embodiment is display 120 of the imaging system 100 of FIG. 1. The medical image may be generated by an ultrasound device, CT device, X-ray device, MRI device, or the like. The image 400 in one example is displayed on a display 402, that in one embodiment is display 120 of the imaging system 100 of FIG. 1. The image 400 includes components 403 including a text box 404, measurements 406 and measurement indicators 408.

In one embodiment, the border of the text box 404 is not on the display 402. In other embodiments, only the measurements 406, and measurement indicators 408 are displayed on the display 402 and they are not within a text box 404.

Measurements 406 and corresponding measurement indicators 408 can include measurement indicia such as numerical values associated with a patient such as fluid levels, fluid concentrations, volume measurements, beats per minute, and the like. These include numerical values that vary or fluctuate over time, or are static. Additionally, measurements 406 and measurement indicators also include object identification such as object borders that include the shape and/or size of an object 412 identified within the medical image 400. Alternatively, the measurement 406 and corresponding measurement indicator 408 can include an identification line that extends across an object 412.

In the exemplary embodiment of FIG. 4, the measurement indicators 408 include measurement indicia 414 and identification lines 416. Alternatively, icons, borders, shapes, or the like could be utilized to represent the different measurements 406. In particular, the identification lines 416 span objects 412 that in this exemplary embodiment are represented by dark spots on the image 400. The objects 412 in different embodiments include organs, fetuses, bones, tissue, and the like. In another example embodiment, the measurement indicator 408 is a border that is placed around each object 412 identified by the measurement device. In example embodiments, measurement indicators 408 are generated utilizing image data and image parameters as described in relation to FIG. 3.

A quality factor indicator 418 is also displayed in the image 400 on the display 402. While illustrated as located adjacent the top left corner of the image, the quality factor indicator 418 can be positioned in other locations on the image 400. The quality factor indicator 418 includes arcuate sections 420A-C. While illustrated as arcuate sections 420A-C, other shapes, or items, such as numbers, letters, or the like, may similarly be utilized.

In this exemplary embodiment, each arcuate section 420A-C is provided with a different color and a text indicator 422A-C that conveys to a user the quality that color represents in the image 400. In this example, the color red has a text indicator 422A of "low", indicating that red presented on the image 400 to identify an image component measurement, trace border, object, or the like has a low quality level, or is poor. Specifically, in one exemplary embodiment the measurement indicators 408 are color-coded to identify the quality of the measurements 406. In the example, the numeral 1 is red, indicating this measurement has a low or poor quality level and enhanced uncertainty is presented. Thus, while the automated measurement device has provided a measurement, a clinician knows the quality, certainty, or fidelity of that measurement is reduced. A closer examination, or decision to obtain an additional image and measurement may result to ensure the measurement is not incorrect, helping prevent an incorrect evaluation. Similarly, frustrations of a clinician can be reduced as the clinician upon seeing an incorrect evaluation can realize the measurement itself was poor quality and that in other instances when the machine imaging is better quality, the measuring device is accurate and an effective tool to be used.

In the example, the second text indicator 422B may indicate "medium" and the color of the second arcuate section 420B may be yellow. In this manner, when yellow is presented on the image 400 to identify a measurement, trace border, object, or the like the quality level of the colored component is merely average. In this exemplary embodiment, both the numeral "2" and "3" may be yellow, indicating the measurement quality is reduced, though not still not that poor of quality level. Thus, depending on the examination, a clinician can decide whether to take an additional image and/or measurement. The third text indicator 422C meanwhile may be "high" while the color of the third arcuate section 420C is green. Thus, again, a clinician is informed that the quality level of the image components, including measurements and objects illustrated in that color are of high quality, certainty, and fidelity. Therefore, when the image results are reviewed and deemed accurate, the clinician gains confidence in the automated measuring device. In addition, the clinician knows less time needs to be spent reviewing the image because of the quality level of the image component, again providing efficiency in the process.

Figure 5:
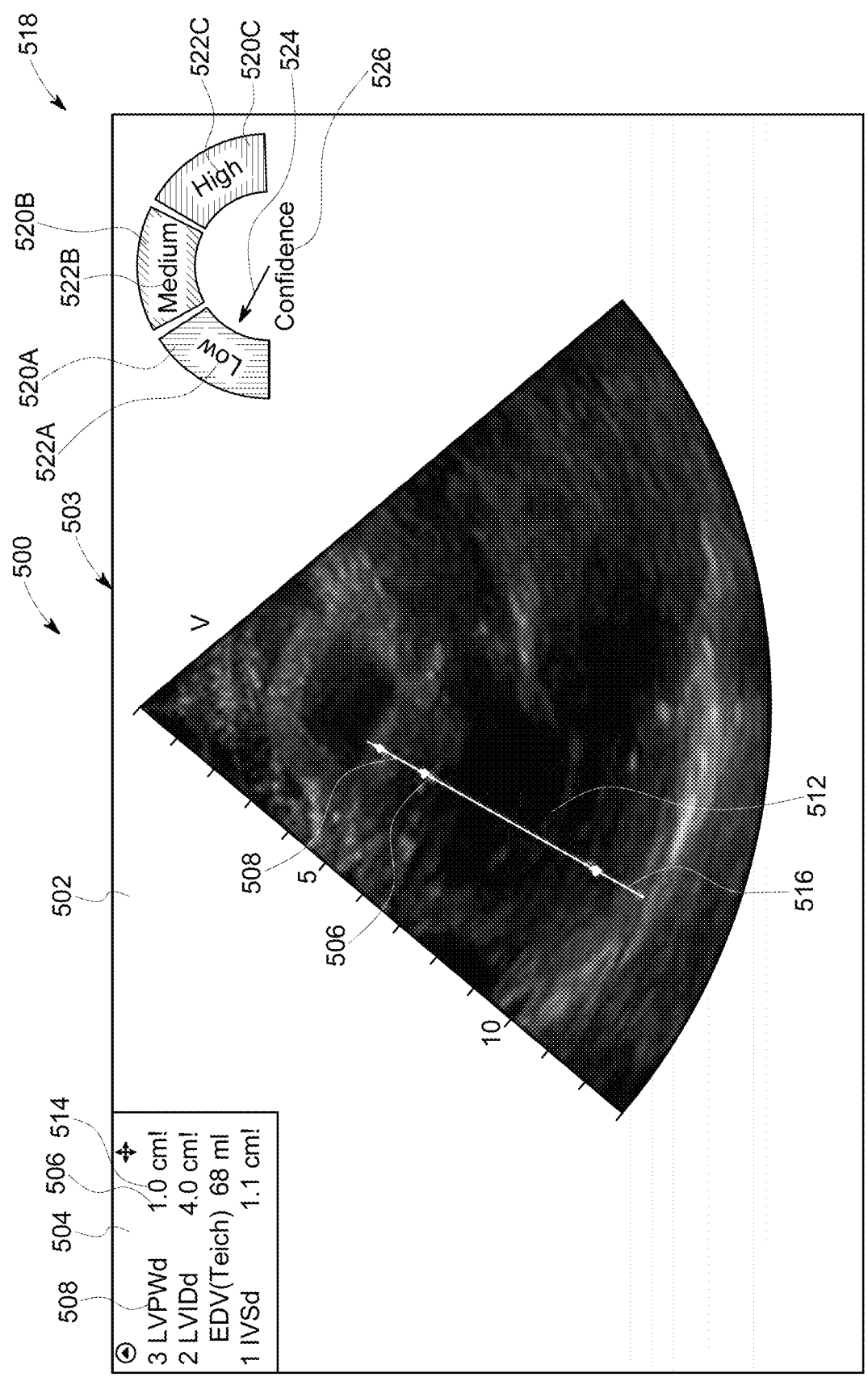
FIG. 5 is a schematic representation of an image in accordance with an embodiment.

FIG. 5 illustrates a schematic representation of a medical image 500 of the patient's anatomy in accordance with an example embodiment. The medical image 500 may be generated by an ultrasound device, CT device, X-ray device, MRI device, or the like. The image 500 in one example is displayed on a display 502, that in one embodiment is display 120 of the imaging system 100 of FIG. 1. The image 500 includes components 503 including a text box 504, measurements 506 and measurement indicators 508.

In one embodiment, the border of the text box 504 is not on the display 502. In other embodiments, only the measurements 506, and measurement indicators 508 are displayed on the display 502 and they are not within a text box 504.

Measurements 506 include numerical values associated with a patient such as fluid levels, fluid concentrations, volume measurements, beats per minute, and the like. These include numerical values that vary or fluctuate over time, or are static. Additionally, measurements 506 also include object identification such as the shape and/or size of an object 512 identified within the medical image 500.

In the exemplary embodiment of FIG. 5, the measurement indicators 508 include measurement indicia 514 and identification lines 516. Alternatively, icons, borders, shapes, or the like could be utilized to represent the different measurements 506. In particular, the identification lines 516 span objects 512 that in this exemplary embodiment are represented by dark spots on the image 500. The objects 512 in different embodiments include organs, fetuses, bones, tissue, and the like. In another example embodiment, the measurement indicator 508 is a border that is placed around each object 512 identified by the measurement device. In example embodiments, measurement indicators 508 are generated utilizing image data and image parameters as described in relation to FIG. 3.

A quality factor indicator 518 is also displayed in the image 500 on the display 502. While illustrated as located in the top right corner of the image, the quality factor indicator 518 can be positioned in other locations on the image 500.

The quality factor indicator 518 includes arcuate sections 520A-C. While illustrated as arcuate sections 520A-C, other shapes, or items, such as numbers, letters, or the like, may similarly be utilized.

In this exemplary embodiment, each arcuate section 520A-C is provided with a different color and a text indicator 522A-C that conveys to a user the quality that color represents in the image 500. In this example, the color red has a text indicator 522A of "low", indicating that red presented on the image 500 to identify an image component measurement, trace border, object, or the like has a low quality level, or is poor. Similarly, the second text indicator 522B can be "medium" and the color of the second arcuate section 520B can be yellow, while the third text indicator 522C is "high" while the color of the third arcuate section 520C is green. Therefore, each color is associated with a different quality level, allowing a clinician to understand the potential accuracy of object identification and measurements.

In an exemplary embodiment an arrow 524 points to the first arcuate section 520A to indicate the quality level of the object identification line 516 that is designating the object 512. Text indicia 526 informs the clinician the quality factor indicator 518 is illustrating a confidence determination of the identification of the object 512 by the object identification line 516. In this example, the confidence level that the dark spot is in fact an object 512 is considered low, indicating to a clinician that closer review of the potential object 512 should be undertaken and there is chance for error in the identification. In other similar measurements, the arrow 524 can therefore point to different arcuate sections 520B-C. In yet another exemplary embodiment, the arrow indicates a quality level of the measurements 506. In another example, the positioning of the arrow 524 is directly proportional to the quality level of a reading or measurement, such that the arrow moves long the arcuate sections 520A-C to indicate increasing and decreasing quality level similar to a speedometer moving in relation to increasing and decreasing speed of a vehicle.

Figure 6:
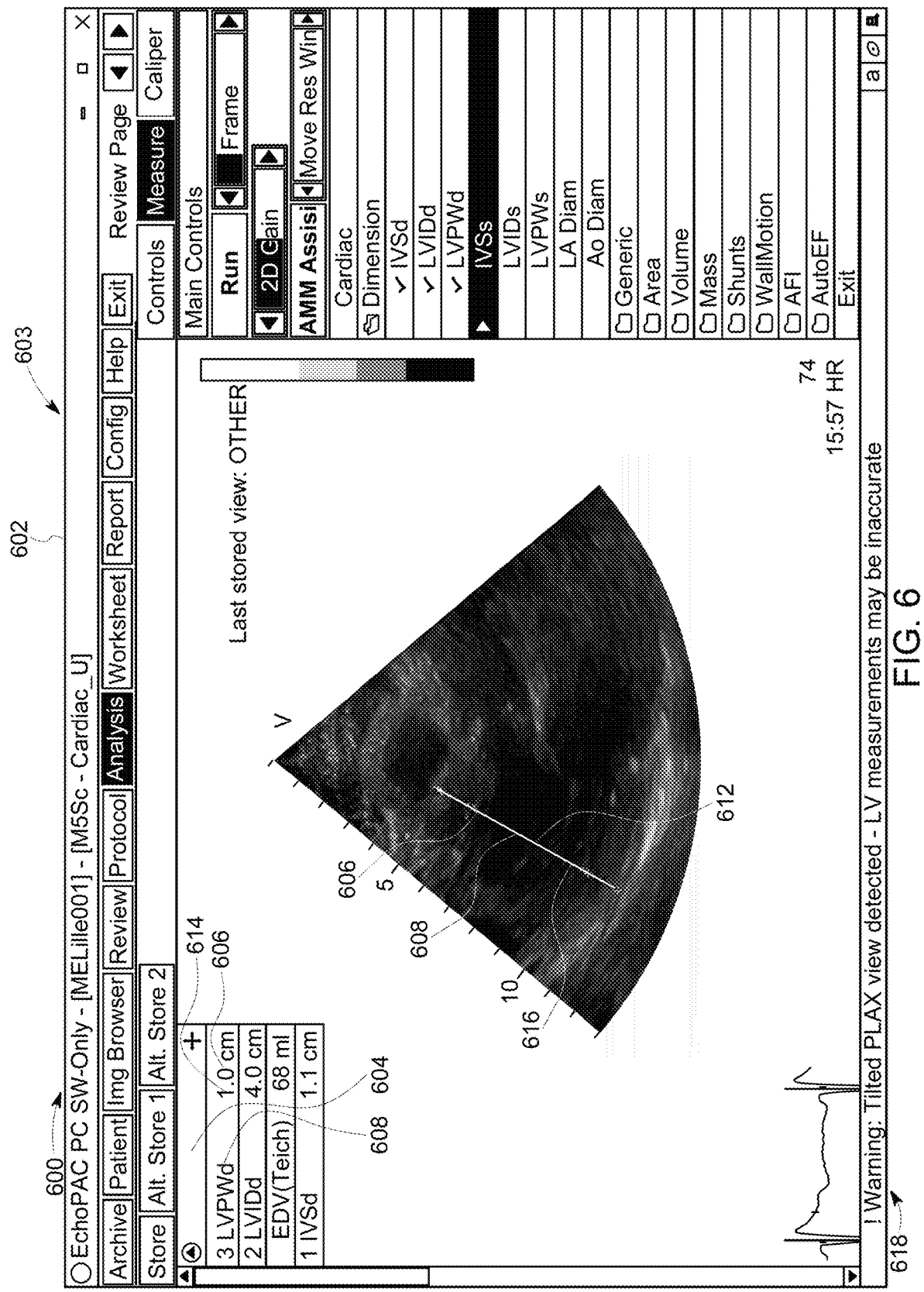
FIG. 6 is a schematic representation of an image in accordance with an embodiment.

FIG. 6 illustrates a schematic representation of a medical image 600 of a patient's anatomy in accordance with an example embodiment. The medical image may be generated by an ultrasound device, CT device, X-ray device, Mill device, or the like. The image 600 in one example is displayed on a display 602, that in one embodiment is display 120 of the imaging system 100 of FIG. 1. The medical image may be generated by an ultrasound device, CT device, X-ray device, MRI device, or the like. The image 600 in one example is displayed on a display 602, that in one embodiment is display 120 of the imaging system 100 of FIG. 1. The image 600 includes components 603 including a text box 604, measurements 606 and measurement indicators 608.

In one embodiment, the border of the text box 604 is not on the display 602. In other embodiments, only the measurements 606, and measurement indicators 608 are displayed on the display 602 and they are not within a text box 604.

Measurements 606 include numerical values associated with a patient such as fluid levels, fluid concentrations, volume measurements, beats per minute, and the like. These include numerical values that vary or fluctuate over time, or are static. Additionally, measurements 606 also include object identification such as the shape and/or size of an object 612 identified within the medical image 600.

In the exemplary embodiment of FIG. 6, the measurement indicators 608 include measurement indicia 614 and identification lines 616. Alternatively, icons, borders, shapes, or the like could be utilized to represent the different measurements 606. In particular, the identification lines 616 span objects 612 that in this exemplary embodiment are represented by dark spots on the image 600. The objects 612 in different embodiments include organs, fetuses, bones, tissue, and the like. In another example embodiment, the measurement indicator 608 is a border that is placed around each object 612 identified by the measurement device. In example embodiments, measurement indicators 608 are generated utilizing image data and image parameters as described in relation to FIG. 3.

A quality factor indicator 618 is also displayed in the image 600 on the display 602. While illustrated as located adjacent the bottom of the image, the quality factor indicator 618 can be positioned in other locations on the image 600. The quality factor indicator 618 in this example embodiment includes indicia, or is a text indicator stating "!Warning Tilted PLAX view detected—LV measurements may be inaccurate". Thus, the clinician is able to observe both the color of the object identification line 616 and view the quality factor indicator 618 to understand a poor reading or measurement has occurred.

Thus, provided are numerous systems utilized to visually represent the quality level of a component within a medial image to a clinician. Such systems are utilized to save time, increase efficiencies, reduce errors, and increase confidence levels of clinicians. Consequently, improved systems are presented.

A method is provided that includes image data, and determining an quality level for a measurement presented in a medical image, the quality level based on the acquired image data. Also included is generating the medical image including a measurement indicator based on the quality level, and displaying the medical image on a display device.

Optionally, the measurement indicator is one of an object border, measurement indicia, or an identification line. Optionally, the method includes determining a color of the measurement indicator based on the quality level. Alternatively the determining the quality level for a measurement presented in a medical image includes determining image parameters from the acquired image data, and analyzing the image parameters to determine the quality level.

Optionally, the analyzing the image parameters includes calculating a standard deviation of the image parameters and comparing the calculated standard deviation to a threshold standard deviation. Also optionally, analyzing the image parameters includes comparing the image parameters to historical image parameters. Alternatively, quality level is based on a threshold amount of image data acquired.

Optionally the method includes automatically selecting a quality factor indicator based on the quality level, and generating the medical image including the quality factor indicator, the quality factor indicator based on the acquired image data and quality level. Alternatively, the quality factor indicator includes a first color and a second color, wherein the first color corresponds to a color of the measurement indicator. Also alternatively, the quality factor indicator includes an arrow that points to the first color.

Optionally, the medical image is one of an ultrasound image, computer tomography image, magnetic resonance imaging image, ultrasound image, X-Ray image, or parasternal long axis view caliper image.

A method is also provided that includes acquiring image data, and determining image parameters from the acquired image data. The method also includes determining a first quality level for a first measurement presented in a medical image, the first quality level based on the determined image parameters, and determining a second quality level for a second measurement presented in the medical image, the second quality level based on the determined image parameters. The method also includes generating a first measurement indicator based on the first quality level, and generating a second measurement indicator based on the second quality level. The method includes generating the medical image including the first measurement indicator and the second measurement indicator, and displaying the medical image on a display device.

Optionally, the first measurement indicator is a first identification line extending across a first object and the second measurement indicator is a second identification line extending across a second object. Also optionally, the first identification line is a first color and the second identification line a second color. The first color can be different than the second color.

Optionally, the first measurement indicator is one of measurement indicia, identification line, or object border and the second measurement indicator is one of measurement indicia, identification line, or object border. Optionally, the method includes automatically selecting a quality factor indicator based on the image parameters, generating the medical image including the quality factor indicator, and displaying the medical image on a display device.

Alternatively, the medical image is one of an ultrasound image, computer tomography image, magnetic resonance imaging image, ultrasound image, X-Ray image, or parasternal long axis view caliper image.

Also provided is a non-transitory computer readable medium having stored thereon, a computer program having at least one code section, said at least one code section being executable by a machine for causing said machine to perform one or more steps where the steps include acquiring image data, and determining a quality level for a measurement presented in a medical image, the quality level based on the acquired image data. Steps also include generating the medical image including a measurement indicator based on the quality level, and displaying the medical image on a display device. Optionally, the measurement indicator includes a color.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. Dimensions, types of materials, orientations of the various components, and the number and positions of the various components described herein are intended to define parameters of certain embodiments, and are by no means limiting and are merely example embodiments. Many other embodiments and modifications within the spirit and scope of the claims will be apparent to those of ordinary skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method comprising:
   acquiring image data;
   determining a quality level for a measurement presented in a medical image, the measurement quality level based on the acquired image data;
   generating the medical image including a measurement indicator based on the quality level;
   displaying the medical image on a display device;
   automatically selecting a quality factor indicator based on the quality level; and
   wherein the quality factor indicator includes a first color and a second color, wherein the first color corresponds to a color of the measurement indicator.

2. The method of claim 1, wherein the measurement indicator is one of an object border, measurement indicia, or an identification line.

3. The method of claim 1, further comprising determining the color of the measurement indicator based on the quality level.

4. The method of claim 1, wherein determining the quality level for the measurement presented in a medical image comprises:
   determining measurement parameters from the acquired image data;
   analyzing the measurement parameters to determine the quality level.

5. The method of claim 4, wherein analyzing the measurement parameters includes calculating a standard deviation of the measurement parameters and comparing the calculated standard deviation to a threshold standard deviation.

6. The method of claim 4, wherein analyzing the measurement parameters includes comparing the measurement parameters to historical parameters.

7. The method of claim 1, wherein the quality level is based on a threshold amount of image data acquired.

8. A method comprising:
   acquiring image data;

determining a quality level for a measurement presented in a medical image, the measurement quality level based on the acquired image data;
generating the medical image including a measurement indicator based on the quality level;
displaying the medical image on a display device;
automatically selecting a quality factor indicator based on the quality level; and
generating the medical image including the quality factor indicator, the quality factor indicator based on the acquired image data and quality level.

9. The method of claim 8, wherein the quality factor indicator includes a first color and a second color, wherein the first color corresponds to a color of the measurement indicator.

10. The method of claim 9, wherein the quality factor indicator includes an arrow that points to the first color.

11. The method of claim 1, wherein the medical image is one of an ultrasound image, computer tomography image, magnetic resonance imaging image, ultrasound image, or X-Ray image.

12. A method comprising:
acquiring image data;
determining image parameters from the acquired image data;
determining a first quality level for a first measurement presented in a medical image, the first quality level based on the determined image parameters;
determining a second quality level for a second measurement presented in the medical image, the second quality level based on the determined image parameters;
generating a first measurement indicator based on the first quality level;
generating a second measurement indicator based on the second quality level;
generating the medical image including the first measurement indicator and the second measurement indicator; and
displaying the medical image on a display device.

13. The method of claim 12, wherein the first measurement indicator is a first identification line extending across a first object and the second measurement indicator is a second identification line extending across a second object.

14. The method of claim 13, wherein the first identification line is a first color and the second identification line a second color.

15. The method of claim 14, wherein the first color is different than the second color.

16. The method of claim 12, wherein the first measurement indicator is one of measurement indicia, identification line, or object border and the second measurement indicator is one of measurement indicia, identification line, or object border.

17. The method of claim 12 further comprising:
automatically selecting a quality factor indicator based on the image parameters;
generating the medical image including the quality factor indicator; and
displaying the medical image on a display device.

18. The method of claim 12, wherein the medical image is one of an ultrasound image, computer tomography image, magnetic resonance imaging image, ultrasound image, or X-Ray image.

19. A non-transitory computer readable medium having stored thereon, a computer program having at least one code section, said at least one code section being executable by a machine for causing said machine to perform one or more steps comprising:
acquiring image data;
determining a quality level for a measurement presented in a medical image, the quality level based on the acquired image data;
generating the medical image including a measurement indicator based on the quality level; and
displaying the medical image on a display device;
wherein a quality factor indicator includes a first color and a second color, wherein the first color corresponds to a color of the measurement indicator.

* * * * *